(12) United States Patent
Müller et al.

(10) Patent No.: US 9,452,233 B2
(45) Date of Patent: Sep. 27, 2016

(54) FRAGRANCE RELEASE SYSTEM WITH VISUAL ENDPOINT INDICATION

(71) Applicant: Symrise AG, Holzminden (DE)

(72) Inventors: Dirk Müller, Dassel (DE); Jennifer Rube, Höxter (DE); Jörn Wiedemann, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 14/643,341

(22) Filed: Mar. 10, 2015

(65) Prior Publication Data

US 2015/0258236 A1    Sep. 17, 2015

(30) Foreign Application Priority Data

Mar. 11, 2014 (EP) ..................... 14158779

(51) Int. Cl.
| | |
|---|---|
| *A61K 8/18* | (2006.01) |
| *A61K 8/00* | (2006.01) |
| *A62B 7/08* | (2006.01) |
| *A61L 9/14* | (2006.01) |
| *A01M 1/20* | (2006.01) |
| *A61L 9/04* | (2006.01) |
| *A61L 9/12* | (2006.01) |
| *A61L 9/01* | (2006.01) |
| *A01N 37/02* | (2006.01) |

(52) U.S. Cl.
CPC ............... *A61L 9/14* (2013.01); *A01M 1/2044* (2013.01); *A01N 37/02* (2013.01); *A61L 9/01* (2013.01); *A61L 9/044* (2013.01); *A61L 9/127* (2013.01); *A61L 2209/11* (2013.01); *A61L 2209/131* (2013.01)

(58) Field of Classification Search
CPC ..... A61L 9/14; A61L 9/01; A61L 2209/131; A61L 9/044; A61L 2209/11; A61L 9/127; A01N 37/02; A01N 25/10; A01M 1/2044; G01N 33/0001

USPC ........................................ 512/22, 1; 422/120
See application file for complete search history.

(56) References Cited

U.S. PATENT DOCUMENTS

| | | | | |
|---|---|---|---|---|
| 8,474,732 | B2 * | 7/2013 | O'Leary | A61L 9/01 239/44 |
| 2011/0135764 | A1 * | 6/2011 | Enan | A01N 65/00 424/745 |
| 2013/0294967 | A1 * | 11/2013 | Blondeau | C11D 3/50 422/5 |
| 2014/0248227 | A1 * | 9/2014 | Doering | A61K 8/34 424/66 |

FOREIGN PATENT DOCUMENTS

WO    2004/087225        * 10/2004
WO    2004/087225 A1    10/2004

OTHER PUBLICATIONS

Dow Corning, Dow Corning 345 Fluid, 1997-2006, Dow Corning, Ref No. 22-1622B-01.*
Schulke, Parmetol DF 35, Jun. 18, 2010, http://www.schuelke.com/download/pdf/PARMETOL_DF_35_ZTM_P_IC_E_EN.PDF.*

\* cited by examiner

*Primary Examiner* — Ling Choi
*Assistant Examiner* — Jessica E Whiteley
(74) *Attorney, Agent, or Firm* — Dilworth & Barrese, LLP (57) ABSTRACT

The proposal is for an active ingredient release system with optical endpoint display, comprising
(a) a container for accommodating the components,
(b) two solvents A and B located therein, which are immiscible or only minorly miscible with one another,
(c) at least one active ingredient which serves as solubilizer for the solvents A and B, and
(d) a mechanism which allows the release of the active ingredient, but restrains the other volatile constituents of the composition.

17 Claims, 4 Drawing Sheets

FRAGRANCE RELEASE SYSTEM WITH VISUAL ENDPOINT INDICATION

FIELD OF THE INVENTION

The invention is located within the field of fragrance release, and relates to a release system where the exhaustion of the active ingredient is indicated by a phase separation, to a corresponding method and to a use.

PRIOR ART

Interior spaces are fragranced and freshened using not only spray systems but also, in particular, evaporation systems. These evaporation systems generally are composed of carrier materials, very simple containers and also very specific containers with accessories, from which the fragrances are delivered to the ambient air. For a long time the concern has been to indicate to the user by a visual signal that the supply of fragrances has been used up.

In U.S. Pat. No. 4,128,508 this task is resolved by means of an indicator system comprising a pH indicator and a slow-evaporation acid or base. As a result of the change in the pH of the fragrance mixture, the altered colour of the pH indicator signals the end of utility.

WO 2003 031 966 A1 describes a system comprising volatile colours. The evaporation of the volatile colour produces a colour change which signals that the fragrances have been used up. A disadvantage of both systems is that the colour change is brought about not by the fragrances themselves, but rather by auxiliaries. In order to achieve a reliable indication of the endpoint of utility, it is necessary to select the fragrances in such a way that they evaporate at exactly the same rate as the auxiliaries. This makes it impossible, or at least considerably more difficult, to produce a creative and complex fragrance.

GB 2444702 A discloses non-aqueous mixtures comprising halochromes, fragrances, non-volatile acids or bases, and highly polar, low-volatility solvents. One disadvantage of such a system are the halochromes used, which possess very reactive atoms, examples being halogen atoms, or reactive groups, examples being amino groups. In addition it is necessary to have acids or bases present that create a favourable medium for reactions. As a result of these adverse conditions, these systems tend towards diverse reactions, meaning that both the fragrances and the halochromes are broken down and that after just a short time a reduction in the intensity of odour, and/or the development of off-odours, and bleaching of the colour as well, are observed. For economic utility, however, there is a need for very long storage stability of the fragrance systems, owing for example to long storage times in the selling of the room fragrances.

One possible alternative might be indicator systems with a so-called "time point", in which a colour change occurs after a certain time has elapsed. These systems, however, are unsuitable for fragrance dispensers, since the evaporation rate is influenced greatly by the ambient temperature and by other factors. Under different conditions, the endpoint will not occur at the same time.

The object of the present invention primarily, therefore, was that of providing fragrance systems with utility endpoint indication that avoid the disadvantages of the prior art as outlined at the outset. The systems ought to be distinguished by the endpoint indication not being brought about through a reduction in the concentration of an auxiliary. A further component object, moreover, was that of providing particularly storage-stable systems.

DESCRIPTION OF THE INVENTION

The invention provides an active ingredient release system with optical endpoint display, comprising
(a) a container for accommodating the components,
(b) two solvents A and B located therein, which are immiscible or only minorly miscible with one another,
(c) at least one active ingredient which serves as solubilizer for the solvents A and B, and
(d) a mechanism which allows the release of the active ingredient, but restrains the other volatile constituents of the composition.

Surprisingly it has been found that special active substances, especially fragrances, are suitable as phase mediators for solvents which are otherwise immiscible or barely miscible with one another. In this way, single-phase systems with high storage stability can be obtained. If the concentration of the active ingredient falls below a critical concentration as a result of evaporation, for example, the substance is no longer able to act as a phase mediator, and separation occurs. This separation then serves as a visual indication that the system has given up the amount of active ingredient it originally contained to the environment—this being referred to as "optical endpoint indication".

The great advantage of this system over the prior art is that the concentration of the active ingredient itself provides a direct endpoint indication—hence it is not necessary to use an auxiliary whose decrease is measured and is required to correlate more or less exactly with the respective concentration of the actual active ingredient (indirect endpoint indication).

For the present invention, moreover, there is also no need for the presence of acids or bases; this fact is massively important particularly for the stability of the composition.

BRIEF DESCRIPTION OF THE DRAWINGS

The present invention will be described in greater detail with reference to the accompanying drawings in which.

DESCRIPTION OF THE PREFERRED EMBODIMENTS

Solvents

The solvents are any compounds in liquid form that are capable of forming a homogeneous phase with the active substance. Where the volatile solvent is held in the container, it may also comprise a known fragrance. As a result of the prevention of the exit of the compound with its own odour performance, the function of the fragrance is confined simply to dissolving the other constituents, and it is used as a solvent in the present invention.

The proportion of the solvents A and B ought preferably to be set such that when the active substance is exhausted, a sufficient amount of the solvents remains so that phase separation is also clearly apparent.

The two solution components should also be selected such that in the presence of the active substance, they separate only when that substance has been almost completely used up.

Predicting the mixing behaviour of the solvents can be done using M numbers (miscibility numbers"), a system developed by Godfrey N. B.[1]. This system consists of 31 classes, divided up between low and high lipophilicity. The classes are called miscibility numbers. Each class consists of solvents exhibiting a similar mixing behaviour with solvents from another class. The solvent is given an M number, and an M number range in which this solvent dissolves.

[1] Godfrey N. B.: "Solvent selection via miscibility number." Chemtech. 6(1972) 359-363

Dipropylene glycol has an M number of 11 and is miscible with solvents in the M range between 1 to 26. A suitable partner solvent for the system ought to have an M number >26.

Propylene carbonate has two M numbers: 9 for the polar range and 17 for the apolar range, and is therefore miscible with solvents in the M range between 2 to 24. A suitable partner solvent for the system ought to have an M number >24.

The volatile fragrance component can be limited to the M number range between 13 and 26. Both solvents selected are to be soluble within this range, i.e. the difference in M numbers between solvent and volatile fragrance component is to be not more than 15, but preferably below 15.

Where no M number is given for a liquid, the number can be determined. For the determination of the M number, the liquid under investigation is added in succession to the standard solvents, and the solubility is assessed after 30 minutes at RT. For each M number class there is a standard solvent—a total of 31 M number classes and standard solvents. In order to calculate the M number, the general rule specified above is employed, which states the following: "If the difference in the M numbers of the two compounds is ≤15, the compounds are miscible with one another." In Table A below, determinations of the M number of phenoxyethanol, propyl acetate and isobutyl isobutyrate are given by way of example:

TABLE A

| M number | Solvent | M number known [1]<br>M number calculated (+15)<br>Phenoxyethanol | 12<br>27 − 15 = 12<br>Propyl acetate | 19<br>4 + 15 = 19<br>Isobutyl isob. | 23<br>8 + 15 = 23 |
|---|---|---|---|---|---|
| 1 | Glycerol | clear solution | 2-phase | 2-phase | |
| 2 | Ethylene glycol | clear solution | 2-phase | 2-phase | |
| 3 | 1,4-Butanediol | clear solution | 2-phase | 2-phase | |
| 4 | 1.2-PROPYLENE GLYCOL | clear solution | clear solution | 2-phase | |
| 5 | DIETHYLENE GLYCOL | clear solution | clear solution | 2-phase | |
| 6 | TRIETHYLENE GLYCOL | clear solution | clear solution | 2-phase | |
| 7 | Tetraethylene glycol | clear solution | clear solution | 2-phase | |
| 8 | Methoxyacetic acid | clear solution | clear solution | clear solution | |
| 9 | Dimethyl sulfoxide | clear solution | clear solution | clear solution | |
| 10 | 2-Pyrrolidone | clear solution | clear solution | clear solution | |
| 11 | DPG | clear solution | clear solution | clear solution | |
| 12 | Phenoxyethanol | clear solution | clear solution | clear solution | |
| 13 | Benzyl alcohol | clear solution | clear solution | clear solution | |
| 14 | Ethanol | clear solution | clear solution | clear solution | |
| 15 | Isopropanol | clear solution | clear solution | clear solution | |
| 16 | Butylglycol | clear solution | clear solution | clear solution | |
| 17 | Cyclohexanone | clear solution | clear solution | clear solution | |
| 18 | 3-Pentanone | clear solution | clear solution | clear solution | |
| 19 | Ethyl acetate | clear solution | clear solution | clear solution | |
| 20 | Dichloromethane | clear solution | clear solution | clear solution | |
| 21 | Ethyl propionate | clear solution | clear solution | clear solution | |
| 22 | Butyl acetate | clear solution | clear solution | clear solution | |
| 23 | Pentyl acetate | clear solution | clear solution | clear solution | |
| 24 | para-Xylene | clear solution | clear solution | clear solution | |
| 25 | Castor oil | clear solution | clear solution | clear solution | |
| 26 | Diisopropyl ether | clear solution | clear solution | clear solution | |
| 27 | Cyclooctene-cis | clear solution | clear solution | clear solution | |
| 28 | Cyclohexane | 2-phase | clear solution | clear solution | |
| 29 | Hexane | 2-phase | clear solution | clear solution | |
| 30 | Tetradecane | 2-phase | clear solution | clear solution | |
| 31 | Heptadecane | 2-phase | clear solution | clear solution | |

Where there is no precise indication concerning the mixing range, it is possible to apply a general rule that states the following: "If the difference in the M numbers of the two compounds is ≥16, the compounds are not miscible with one another."

The difference in the M numbers of the solvents selected is therefore to be at least 16, but preferably greater than 16.

If the difference in the M numbers is exactly 16, it is possible that the solvents dissolve at an ambient temperature >25° C. and extremely likely that they dissolve at an ambient temperature >75° C. Such systems are possibly suitable for use at room temperature, but are to be avoided for applications at higher temperatures, as in the case, for example, of a dishwasher air freshener, or an electric air freshener, where the composition is heated for enhanced evaporation.

The preferred solvents comprise vegetable oils, $C_6$-$C_{22}$ fatty acid $C_1$-$C_6$ alkyl esters, $C_1$-$C_6$ alkyl carbonates, $C_2$-$C_4$ alkylene glycols and also siloxanes, more particularly esters of lauric acid, myristic acid and stearic acid with ethanol, propanol or isopropyl alcohol, ethylene carbonate, propylene carbonate, butylene carbonate, ethylene glycol, propylene glycol, diethylene glycol, dipropylene glycol and decamethylcyclopentasiloxane, it being possible for the mixing ratio to be situated in a range between about 40:60 and 60:40 parts by weight and preferably about 50:50 parts by weight.

An essential advantage of the invention is the suitability of vegetable oils as solvents for the system described. The vegetable oils are particularly eco-friendly and unobjectionable from the standpoint of health. The selection of compounds unobjectionable to humankind and environment that are used in this indicator system is not confined only to the vegetable oils. Many possibilities exist for compiling the indicator system only from compounds which in accordance with Directive 67/548/EEC are not hazardous products and do not require any special hazard warnings for humankind and environment.

Particularly preferred solvent systems with vegetable oils are dipropylene glycol/rapeseed oil, triacetin/sunflower oil, dipropylene glycol/sunflower oil and triacetin/rapeseed oil.

The solvent systems identified above, together with food dyes and a natural fragrance oil as active substance, are able to form a particularly eco-friendly air freshener.

Further preferred solvent systems are, for instance, decamethylcyclopentasiloxane/dipropylene glycol; isopropyl myristate/propylene carbonate;

and also glycerol/Symfresh NX; propylene 1,2-glycol/benzyl benzoate; propylene carbonate/dioctyl adipate; triethyl citrate/decamethylcyclopentasiloxane (DOW CORNING 245 FLUID); polyethylene glycol 400 (Polydiol 400)/medical white oil (Pionier CP65).

Further suitable solvent pairings are compiled, where the solvent A is able to form a pairing with the arbitrary solvent B from the same table section. The table sections are divided according to the M number of the solvent A.

By way of example for the $2^{nd}$ table section with solvent A=2:

Ethylene glycol as solvent A with M=2 is able to form a suitable pairing with any solvent B in the M number range from 19 to 21. The same applies to 1,2,6-hexanetriol and 2-hydroxyethyl carbonate. The table section for solvent A=2 therefore contains 3×14=42 suitable solvent pairings. A multiplicity of suitable solvent pairings are identified overall in Table B.

TABLE B

| M number solv. A = 1 | Solvent A | Solvent B | M number solv. 18 ≤ B ≤ 20 |
|---|---|---|---|
| | Glycerol | SymFresh NX | |
| | | Diethyl carbonate | |
| | | Dimethyl adipate | |
| | | Propylene glycol diacetate | |
| | | Benzyl alcohol | |
| | | Triacetin | |
| | | Triethyl citrate | |
| | | Dimethyl phthalate | |
| | | Diethyl phthalate | |
| M number solv. A = 2 | Solvent A | Solvent B | M number solv. 19 ≤ B ≤ 21 |
| | Ethylene glycol | Dimethyl adipate | |
| | 1,2,6-Hexanetriol | Diethyl carbonate | |
| | 2-Hydroxyethyl carbamate | Diallyl adipate | |
| | | Diethyl adipate | |
| | | Ethyl benzoate | |
| | | Methyl isoamyl ketone | |
| | | Propylene glycol diacetate | |
| | | Methyl isobutyl ketone | |
| | | Benzyl alcohol | |
| | | Benzyl benzoate | |
| | | Diethyl phthalate | |
| | | Triacetin | |
| | | Triethyl citrate | |
| | | Dimethyl phthalate | |
| M number solv. A = 3 | Solvent A | Solvent B | M number solv. 20 ≤ B ≤ 22 |
| | 1,3-Propanediol | Dibutyl phthalate | |
| | 1,4-Butanediol | Dimethyl sebacate | |
| | 1,5-Pentanediol | Diallyl adipate | |
| | 2-Butene-1,4-diol | Ethyl benzoate | |
| | 2-Hydroxypropyl carbamate | Benzyl alcohol | |
| | Glycerol carbonate | Dibutyl maleate | |
| | | 2-Octanone | |
| | | 3-Heptanone | |
| | | Allyl ether | |
| | | Benzyl benzoate | |
| | | Diethyl phthalate | |

TABLE B-continued

Solvent pairings

| M number solv. A = 4 | Solvent A | Solvent B | M number solv. 21 ≤ B ≤ 23 |
|---|---|---|---|
| | 1,2-Propanediol<br>1,3-Butanediol | Dimethyl sebacate<br>Dipropyl carbonate<br>Ethyl benzoate<br>2-Octanone<br>3-Heptanone<br>Dibutyl maleate<br>Benzyl benzoate<br>Diallyl adipate | |

| M number solv. A = 5 | Solvent A | Solvent B | M number solv. 22 ≤ B ≤ 24 |
|---|---|---|---|
| | 2,5-Hexanediol<br>3-Methoxy-1,2-propanediol<br>Diethylene glycol | Dioctyl phthalate<br>Dimethyl sebacate<br>Dibutyl maleate<br>Dipropyl carbonate<br>2-Octanone<br>3-Heptanone | |

| M number solv. A = 6 | Solvent A | Solvent B | M number solv. 23 ≤ B ≤ 25 |
|---|---|---|---|
| | 1,2-Butanediol<br>Triethylene glycol<br>Ethylene carbonate<br>Hydroxypropyl maleate<br>Hydroxypropyl maleate | Dioctyl phthalate<br>Castor oil<br>Dipropyl carbonate<br>Diisobutyl ketone<br>Diisopropyl ketone<br>Diisopropylbenzene<br>1,2-Dibutoxyethane<br>1,3-Pentadiene<br>sec-Amylbenzene<br>ABALYN D-E | |

| M number solv. A = 7 | Solvent A | Solvent B | M number solv. 24 ≤ B ≤ 26 |
|---|---|---|---|
| | ETHYLENE CARBONATE<br>Pentaethylene glycol<br>Tetraethylene glycol | Dioctyl phthalate<br>Castor oil<br>Methyl oleate<br>Didecyl phthalate<br>Dioctyl adipate<br>HERCOLYN D-E<br>Diethoxydimethylsilane<br>Dimethoxydimethylsilane<br>Diisopropylbenzene<br>1,2-Dibutoxyethane<br>1,3-Pentadiene<br>sec-Amylbenzene<br>ABALYN D-E<br>4-Vinylcyclohexene<br>Cyclohexene<br>Dicyclopentadiene<br>Methyl stearate<br>Pentyl ether<br>2-Octyldodecanol | |

| M number solv. A = 8 | Solvent A | Solvent B | M number solv. 25 ≤ B ≤ 27 |
|---|---|---|---|
| | 1-(2-Hydroxyethoxy)-2-propanol<br>Acetol (hydroxy acetone)<br>Methyl cyanoacetate | Castor oil<br>Methyl oleate<br>Methyl stearate<br>Didecyl phthalate<br>Dioctyl adipate<br>Diisopropylbenzene<br>1,7-Octadiene<br>sec-Amylbenzene<br>1,3-Pentadiene<br>4-Vinylcyclohexene<br>Cyclohexene<br>Dicyclopentadiene<br>Diethoxydimethylsilane<br>Dimethoxydimethylsilane<br>1,2-Dibutoxyethane<br>cis-4-Methyl-2-pentene | |

TABLE B-continued

| Solvent pairings |
|---|
| Cyclooctene |
| 2,2,4-Trimethyl-2-pentene |
| 2,4,4-Trimethyl-1-pentene |
| ABALYN D-E |
| HERCOLYN D-E |
| 2-Octyldodecanol |
| Isopropyl myristate |
| Isopropyl palmitate |
| Ethyl myristate |
| Vegetable oil triglyceride |

| M number solv. A = 9 | Solvent A | Solvent B | M number solv. 26 ≤ B ≤ 28 |
|---|---|---|---|
| | PROPYLENE CARBONATE<br>Dimethyl sulfoxide<br>Ethylene glycol bismethoxyacetate | Dioctyl adipate<br>Methyl oleate<br>Methyl stearate<br>Butyl oleate<br>Isopropyl myristate<br>Isopropyl palmitate<br>Ethyl myristate<br>Vegetable oil<br>preferred vegetable oil is rapeseed oil<br>preferred vegetable oil is sunflower oil<br>preferred vegetable oil is olive oil<br>preferred vegetable oil is almond oil<br>preferred vegetable oil is soyabean oil<br>preferred vegetable oil is linseed oil<br>Dicyclopentadiene<br>4-Vinylcyclohexene<br>2,2,4-Trimethyl-2-pentene<br>2,4,4-Trimethyl-1-pentene<br>Pentyl ether<br>1,7-Octadiene<br>Cyclooctene<br>1-Octene<br>1-Heptene<br>Didecyl phthalate<br>Diethoxydimethylsilane<br>Dimethoxydimethylsilane<br>HERCOLYN D-E<br>2-Octyldodecanol | |

| M number solv. A = 10 | Solvent A | Solvent B | M number solv. 27 ≤ B ≤ 29 |
|---|---|---|---|
| | 1,2-Butylene carbonate<br>Acetol acetate | Butyl oleate<br>1-Hexadecene<br>Isopropyl myristate<br>ISOPROPYL PALMITATE<br>ETHYL MYRISTATE<br>Vegetable oil<br>preferred vegetable oil is rapeseed oil<br>preferred vegetable oil is sunflower oil<br>preferred vegetable oil is olive oil<br>preferred vegetable oil is almond oil<br>preferred vegetable oil is soyabean oil<br>preferred vegetable oil is linseed oil<br>Coconut oil<br>1,7-Octadiene<br>1-Tetradecene<br>1-Decene<br>1-Dodecene<br>Bicyclohexyl<br>Cyclooctane<br>Cyclooctene<br>1-Octene<br>1-Heptene<br>1-Octene<br>Decane<br>Dodecane<br>2,2,4-Trimethyl-2-pentene<br>2,4,4-Trimethyl-1-pentene<br>Octane<br>Decamethylcyclopentasiloxane (DOW CORNING 245 FLUID)<br>Tetrapropylene<br>Triisobutylene | |

TABLE B-continued

Solvent pairings

Hexamethyldisiloxane

| M number solv. A = 11 | Solvent A | Solvent B | M number solv. 28 ≤ B ≤ 30 |
|---|---|---|---|
| | Triacetin | Butyl oleate | |
| | Dipropylene glycol | Vegetable oil | |
| | Dimethyl malonate | preferred vegetable oil is rapeseed oil | |
| | | preferred vegetable oil is sunflower oil | |
| | | preferred vegetable oil is olive oil | |
| | | preferred vegetable oil is almond oil | |
| | | preferred vegetable oil is soyabean oil | |
| | | 1-Hexadecene | |
| | | 1-Tetradecene | |
| | | Decamethylcyclopentasiloxane (e.g. DOW CORNING 245 FLUID) | |
| | | Coconut oil | |
| | | Hexamethyldisiloxane | |
| | | 1-Decene | |
| | | 1-Dodecene | |
| | | Bicyclohexyl | |
| | | Cyclooctane | |
| | | Decane | |
| | | Dodecane | |
| | | 1-Octene | |
| | | 1-Heptene | |
| | | Octane | |
| | | Decamethylcyclopentasiloxane (e.g. DOW CORNING 245 FLUID) | |
| | | Tetrapropylene | |
| | | Triisobutylene | |
| | | 1-Octadecene | |
| | | Hexadecane | |
| | | Tetradecane | |
| | | Hexamethyldisiloxane | |
| | | Heptadecane | |
| | | Ecolane 130 AN | |
| | | Isopar V | |

| M number solv. A = 12 | Solvent A | Solvent B | M number solv. 29 ≤ B ≤ 31 |
|---|---|---|---|
| | Dimethyl phthalate | Decamethylcyclopentasiloxane (e.g. DOW CORNING 245 FLUID) | |
| | Tripropylene glycol | 1-Decene | |
| | Triethyl citrate | 1-Dodecene | |
| | 2-Phenoxyethanol | 1-Hexadecene | |
| | Diethylene glycol monomethyl ether | Coconut oil | |
| | Diethylene glycol diacetate | Cyclooctane | |
| | Diethyl sulphate | Bicyclohexyl | |
| | Dimethyl maleate | Hexamethyldisiloxane | |
| | Ethylene glycol monopropyl ether | Decane | |
| | Ethylene glycol diacetate | Dodecane | |
| | Phenylacetonitrile | Octane | |
| | 2,3-Butanedione | 1-Tetradecene | |
| | 2,4-Pentanedione | Tetrapropylene | |
| | 2,5-Hexanedione | Triisobutylene | |
| | | 1-Octadecene | |
| | | Hexadecane | |
| | | Tetradecane | |
| | | Heptadecane | |
| | | Ecolane 130 AN | |
| | | Isopar V | |
| | | Medical white oil (e.g. Pionier CP 65) | |
| | | Mineral oil | |

| M number solv. A = 13 | Solvent A | Solvent B | M number solv. 30 ≤ B ≤ 31 |
|---|---|---|---|
| | 1-Phenoxy-2-propanol | 1-Octadecene | |
| | Diethylene glycol monoethyl ether | Hexadecane | |
| | Diethyl phthalate (C8 dicarboxylic ester) | Tetradecane | |
| | Ethyl acetoacetate | medical white oil (e.g. Pionier CP 65) | |
| | Ethylene glycol monomethyl ether | Mineral oil | |
| | Glycidyl phenyl ether | Heptadecane | |
| | Methyl methoxyacetate | Ecolane 130 AN | |

TABLE B-continued

Solvent pairings

| | | |
|---|---|---|
| Triethylene glycol monomethyl ether | Isopar V | |
| 2-Allyloxyethanol | | |
| 2-Methoxyethanol | | |

| M number solv. A = 14 | Solvent A | Solvent B | M number solv. B = 31 |
|---|---|---|---|
| | Hexanediol | medical white oil (e.g. Pionier CP 65) | |
| | POLYDIOL 400 (Polyethylene glycol 400) | Paraffin oil, white | |
| | Propylene glycol diacetate | Mineral oil | |

The mixing ratio may likewise again lie in the range between about 40:60 and 60:40 parts by weight, and may preferably be about 50:50 parts by weight.

The pH of the systems of the invention should be set preferably in the neutral range. The pH of the mixture of the invention is preferably about 5 to about 9 and more preferably 6 to 8. The solvent mixture may optionally comprise stabilizers. Stabilizers in accordance with the invention are preferably light stabilizers, antioxidants and emulsifiers.

Active Ingredients

The active ingredients of the present invention are preferably fragrances. Accordingly, the systems of the invention also preferably constitute dispensers which release active odour-masking, odour-neutralizing or insect-repelling ingredients, including active antimicrobial ingredients.

Fragrances

Fragrances and perfume oils which are employed with preference and may be incorporated into the products are not subject to any restrictions at all. Hence as fragrances it is possible to use individual odorant compounds, either synthetic or natural compounds of the class of esters, ethers, aldehydes, ketones, alcohols, hydrocarbons, acids, carbonic esters, aromatic hydrocarbons, aliphatic hydrocarbons, saturated and/or unsaturated hydrocarbons, and mixtures thereof. Fragrance aldehydes or fragrance ketones used may be all customary fragrance aldehydes and fragrance ketones which are typically employed in order to bring about a pleasant fragrance sensation. Suitable fragrance aldehydes and fragrance ketones are common knowledge to the skilled person. The fragrance ketones may encompass all ketones which are able to impart a desired fragrance or a sensation of freshness. Mixtures of different ketones may also be used. For example, the ketone may be selected from the group consisting of buccoxime, isojasmone, methyl beta-naphthyl ketone, musk indanone, Tonalid/musk plus, alpha-damascone, beta-damascone, delta-damascone, isodamascone, damascenone, damarose, methyl dihydrojasmonate, menthone, carvone, camphor, fenchone, alpha-ionone, beta-ionone, dihydro-beta-ionone, gamma-methylionone (so-called), fleuramone, dihydrojasmone, cisjasmone, Iso-E-Super, methyl cedrenyl ketone or methyl-cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyloctenone, Freskomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6 (2)-yl)-1-propanone, 4-(4-hydroxy-3-methoxyphenyl)-2-butanone, 2-acetyl-3,3-dimethylnorbornane, 6,7-dihydro-1,1,2,3,3-pentamethyl-4(5H)-indanone, 4-damascol, dulcinyl or cassione, gelsone, hexalone, isocyclemone E, methylcyclocitrone, methyl-lavender ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from alpha-damascone, delta-damascone, isodamascone, carvone, gamma-methylionone, Iso-E-Super, 2,4,4,7-tetramethyloct-6-en-3-one, benzylacetone, beta-damascone, damascenone, methyl dihydrojasmonate, methylcedrylone, hedione and mixtures thereof.

Suitable fragrance aldehydes may be any desired aldehydes which, in the same way as for the fragrance ketones, impart a desired odour or a sensation of freshness. Again they may be individual aldehydes or aldehyde mixtures. Suitable aldehydes are, for example, melonal, triplal, ligustral, adoxal, anisaldehyde, cymal, ethylvanillin, florhydral, floralozone, helional, heliotropin, hydroxycitronellal, koavone, lauryl aldehyde, canthoxal, lyral, lilial, adoxal, anisaldehyde, cumal methylnonylacetaldehyde, citronellal, citronellyloxyacetaldehyde, cyclamen aldehyde, bourgeonal, p,t-bucinal, phenylacetaldehyde, undecylenealdehyde, vanillin; 2,6,10-trimethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4-isopropylbenzyl aldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal; 4-(tricyclo[5.2.1.0$^{(2,6)}$] decylidene-8)-butanal; octahydro-4,7-methano-1H-indenecarboxaldehyde; 3-ethoxy-4-hydroxybenzaldehyde, para-ethyl-alpha,alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butylphenyl)propanal, 3-(4-ethylphenyl)-2,2-dimethylpropanal, 3-(4-methoxyphenyl)-2-methylpropanal, methylnonylacetaldehyde, 2-phenylpropan-1-al, 3-phenylprop-2-en-1-al, 3-phenyl-2-pentylprop-2-en-1-al, 3-phenyl-2-hexylprop- 2-enal, 3-(4-isopropylphenyl)-2-methylpropan-1-al, 3-(4-ethylphenyl)-2,2-dimethylpropan-1-al, 3-(4-tert-butylphenyl)-2-methylpropanal, 3-(3,4-methylenedioxyphenyl)-2-methylpropan-1-al, 3-(4-ethylphenyl)-2,2-dimethylpropanal, 3-(3-isopropylphenyl) butan-1-al, 2,6-dimethylhept-5-en-1-al, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexenecarboxyaldehyde, 7-hydroxy-3,7-dimethyloctanal; trans-4-decenal, 2,6-nonadienal, para-tolylacetaldehyde; 4-methylphenylacetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, octanal, 2-methyloctanal, alpha-methyl-4-(1-methylethyl)benzeneacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde, 4-methoxybenzaldehyde, 3-methoxy-4-hydroxybenzaldehyde, 3-ethoxy-4-hydroxybenzaldehyde, 3,4-methylenedioxybenzaldehyde and 3,4-dimethoxybenzaldehyde and mixtures thereof. As observed by way of example above, the fragrance aldehydes and fragrance ketones may have an aliphatic, cycloaliphatic, aromatic, ethylenically unsaturated structure or a combination of these structures. There may also be further heteroatoms or polycyclic structures present. The structures may have suitable substituents such as hydroxyl groups or amino groups. For further suitable fragrances, selected from aldehydes and ketones, reference is made to Steffen Arctander, published 1960 and 1969 respectively, reprinted 2000 ISBN: Aroma Chemicals Vol. 1: 0-931710-37-5, Aroma Chemicals Vol. 2: 0-931710-38-3.

Suitable odorant compounds of the ester type are, for example, benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethyl methyl phenylglycinate, allyl cyclohexylpropionate, styrallyl propionate, benzyl salicylate, cyclohexyl salicylate, floramate, melusate and jasmacyclate. Odorant compounds of the hydrocarbon type are, for example, terpenes such as limonene and pinene. Suitable fragrances of the ether type are, for example, benzyl ethyl ether and ambroxane. Suitable fragrance alcohols are, for example, 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethylvanilin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol; if two or more fragrance alcohols are present, they may be selected independently of one another.

Fragrances and perfume oils may also be natural odorant mixtures, such as those obtainable from plant sources, examples being pine, citrus, jasmine, patchouli, rose or ylang-ylang oil. Likewise suitable are clary sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil. Essential oils such as angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjan balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, amber seed oil, myrrh oil, clove oil, neroli oil, niaouli oil, olibanum oil, oregano oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil and cypress oil.

Likewise suitable as fragrance are what are called fragrance precursors (pro-drugs). This class of compounds comprises compounds which release a desired odour molecule and/or fragrance molecule through the breaking of a chemical bond, by hydrolysis, for example. To form a fragrance precursor, typically, a desired fragrance raw material is joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of the change in pH, for example (through perspiration during wear, for example), atmospheric humidity, heat and/or sunlight during storage or during drying on a washing line.

The fragrance raw material for use in fragrance precursors typically comprises saturated or unsaturated volatile compounds containing an alcohol, an aldehyde and/or a ketone group. The fragrance raw materials that are useful herein include any pleasingly odorous substances or mixtures of substances which have already been described above.

Particularly advantageous fragrance precursors which can be used conform to the formula (I)

$$R-C(OR^1)(OR^2)-OR^3 \qquad (I)$$

in which R is hydrogen, linear $C_1$-$C_8$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$, $R^2$ and $R^3$ independently are linear, branched or substituted $C_1$-$C_{20}$ alkyl; linear, branched or substituted $C_2$-$C_{20}$ alkenyl;

substituted or unsubstituted, cyclic $C_3$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_6$-$C_{32}$ aryloxy; substituted or unsubstituted $C_6$-$C_{40}$ alkyleneoxyaryl; $C_6$-$C_{40}$ oxyalkylenearyl and mixtures thereof. The use of such substances, especially in (preferably water-insoluble) microcapsules, corresponds to one preferred embodiment of the invention.

Further particularly advantageous fragrance precursors which can be used are acetals or ketals, preferably conforming to the formula (II)

$$R\!-\!C(R^1)(OR^3)\!-\!OR^2 \qquad (II)$$

in which R is linear $C_1$-$C_{20}$ alkyl, branched $C_3$-$C_{20}$ alkyl, cyclic $C_6$-$C_{20}$ alkyl, branched cyclic $C_6$-$C_{20}$ alkyl, linear $C_2$-$C_{20}$ alkenyl, branched $C_3$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$ is hydrogen or R; $R^2$ and $R^3$ each independently of one another are selected from the group consisting of linear $C_1$-$C_{20}$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, $C_6$-$C_{20}$ aryl, substituted $C_7$-$C_{20}$ aryl and mixtures thereof. The use of such substances, especially in (preferably water-insoluble) microcapsules, corresponds to one preferred embodiment of the invention.

Further particularly advantageous fragrance precursors which can be used conform to the formula (III)

$$R^4O\!-\!C(OR^1)(OR^3)\!-\!OR^2 \qquad (III)$$

in which $R^1$, $R^2$, $R^3$ and $R^4$ independently of one another are linear, branched or substituted $C_1$-$C_{20}$ alkyl; linear, branched or substituted $C_2$-$C_{20}$ alkenyl; substituted or unsubstituted, cyclic $C_5$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_6$-$C_{32}$ aryloxy; substituted or unsubstituted $C_6$-$C_{40}$ alkyleneoxyaryl; $C_6$-$C_{40}$ oxyalkylenearyl; and mixtures thereof. The use of such substances, especially in (preferably water-insoluble) microcapsules, corresponds to one preferred embodiment of the invention.

It is particularly preferable for the odorants used to comprise silicic ester mixtures. Silicic esters are described for example by the formula (IV)

$$R\!-\!(\!-\!O\!-\!Si(OR)_2\!-\!)_n\!-\!OR \qquad (IV)$$

where R independently at each occurrence is selected from the group containing H, the straight-chain or branched, saturated or unsaturated, substituted or unsubstituted $C_1$-$C_6$ hydrocarbon radicals and the fragrance alcohol radicals and/or biocide alcohol radicals, and m adopts values from the range from 1 to 20 and n adopts values from the range from 2 to 100. The silicic esters of the formula (IV) preferably comprise at least one fragrance alcohol residue and/or biocide alcohol residue.

Particularly suitable fragrance precursors are reaction products of compounds which comprise at least one primary and/or secondary amine group, as for example an aminofunctional polymer, more particularly an amino-functional silicone, and a fragrance constituent which is selected from ketone, aldehyde and mixtures thereof.

Particularly preferred is a solvent/active ingredient combination which as solvent mixture comprises propylene carbonate/isopropyl alcohol, in combination with at least one of the active ingredients citral, phenyl acetate, limonene and hexyl acetate.

Active Antimicrobial Ingredients

Active antimicrobial ingredients, which may likewise be used as active substances and released via the systems of the invention, include, for example, all suitable substances active against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynylbutyl carbamate, chlorhexidine, 3,4,4'-trichlorocarbanilide (TTC), antibacterial odorants, thymol, thyme oil, eugenol, clove oil, menthol, mint oil, farnesol, phenoxyethanol, glyceryl monocaprate, glyceryl monocaprylate, glyceryl monolaurate (GML), diglyceryl monocaprate (DMC), N-alkyl amides of salicylic acid such as, for example, N-n-octylsalicylamide or N-n-decylsalicylamide.

Use may also be made, however, of enzyme inhibitors such as esterase inhibitors, for example. These are preferably trialkyl citrates such as trimethyl citrate, tripropyl citrate, triisopropyl citrate, tributyl citrate and, in particular, triethyl citrate (Hydagen® CAT). The compounds inhibit enzyme activity and thereby reduce development of odour. Further substances contemplated as esterase inhibitors are sterol sulphates or sterol phosphates, such as lanosterol, cholesterol, campesterol, stigmasterol and sitosterol sulphate and phosphate, respectively, dicarboxylic acids and their esters, such as, for example, glutaric acid, monoethyl glutarate, diethyl glutarate, adipic acid, monoethyl adipate, diethyl adipate, malonic acid and diethyl malonate, hydroxycarboxylic acids and their esters such as, for example, citric acid, malic acid, tartaric acid or diethyl tartrate, and also zinc glycinate.

Also suitable, lastly, are odour absorbers, which are able to take up and largely hold odour-forming compounds. They reduce the partial pressure of the individual components and hence also lower their propagation rate. It is important that in this case perfumes must remain unaffected. Odour absorbers have no activity against bacteria. Their principal constituent is, for example, a complex zinc salt of ricinoleic acid, or specific, largely odourneutral fragrances, known to the skilled person as "fixatives", such as extracts of labdanum or styrax, or certain abietic acid derivatives, for example. Acting as odour masks are odorants or perfume oils which, in addition to their function as odour-masking agents, impart their respective fragrance note to the deodorants. Examples that may be given of perfume oils include mixtures of natural and synthetic odorants. Natural odorants are extracts of blossoms, stems and leaves, fruits, fruit husks, roots, woods, herbs and grasses, needles and branches, and also resins and balsams. Also suitable are animal raw materials, such as civet and castoreum, for example. Typical synthetic odorant compounds are products of the ester, ether, aldehyde, ketone, alcohol and hydrocarbon types. Examples of ester-type odorant compounds are benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether; the aldehydes include, for example, linear alkanals having 8 to 18 carbon atoms, citral, citronellal, citronellyloxyacetaldehyde, cyclamenaldehyde, hydroxycitronellal, lilial and bourgeonal; the ketones include, for example, the ionones and methyl cedryl ketone; the alcohols include anethole, citronellol, eugenol, isoeugenol, geraniol, linalool, phenylethyl alcohol and terpineol; the hydrocarbons include primarily the terpenes and balsams. Preference, however, is given to using mixtures of different odorants, which together generate an appealing fragrance note. Essential oils of relatively low volatility as well, usually used as aroma components, are suitable as perfume oils, examples being sage oil, camomile oil, clove oil, melissa oil, mint oil, cinnamon leaf oil, lime blossom oil, juniper berry oil, vetiver oil, olibanum oil, galbanum oil, labdanum oil and lavendula oil. Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxane, indole, hedione, sandelice, citrus oil, mandarin oil, orange oil, allyl amyl glycolate, cyclovertal, lavendula oil, clary sage oil, β-damascone, geranium oil, bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilate, irityl and floramate, alone or in mixtures.

Insect Repellents

Also contemplated, as a further group of active substances, are compounds which repel insects, such as, for example, N,N-diethyl-m-toluamide, 1,2-pentanediol or ethyl butylacetylaminopropionate.

Evaporation Rate

In another preferred embodiment of the invention, the evaporation rate V of the active substances, and especially of the fragrances, is at least twice the evaporation rate of the solvents. The evaporation rate V for the purposes of the invention means the mass loss per unit surface area within a defined time period under defined and identical conditions:

$$V = \frac{m(t0) - m(t)}{A_P * t}$$

In the equation above, m (t0) denotes the mass of the sample at the start of the test, m(t) denotes the mass of the sample after evaporation time t, $A_P$ denotes the surface area of the solvent or of the fragrances, and t denotes the time period within which evaporation has taken place. In order to ensure comparability, $A_P$, t and m (t0) are constant. As a reference, the following method is employed: 40 mg of the solvent or fragrances are applied to a flat DVS 1000 sample pan from SMS Surface Measurement Systems UK. The mass losses of the sample are ascertained at 40° C.

The membrane permeation coefficient of the fragrances is preferably at least twice the membrane permeation coefficient of the solvents. The membrane permeation coefficient M for the purposes of the invention means the mass flow of the solvents or fragrances per unit area through the semi-permeable membrane.

$$M = \frac{m(t0) - m(t)}{A_M * t}$$

In the equation above, m (t0) denotes the mass of the sample at the start of testing, m(t) denotes the mass of the sample after evaporation time t, $A_M$ denotes the surface area of the membrane, and t denotes the time period within which evaporation has taken place. In order to ensure comparability, $A_M$, t and m (t0) are constant.

As a reference for determining the membrane permeation coefficient M, the following method is employed: 20 g of solvent or fragrances are placed in a glass Petri dish. The semi-permeable membrane is adhered to the edge of the Petri dish in such a way that the opening of the Petri dish is completely covered by the membrane, and the adhesive seals the assembly in such a way that the solvent or fragrances are unable to escape at the sides. After 2 weeks of storage at 25° C., determinations are made of the mass loss and M in accordance with the equation.

Dyes

In certain cases it is desirable for the systems of the invention to receive assistance with regard to the visual perception of the endpoint indication by phase separation. This can be done by addition of dyes.

Apart from solubility in the respective component of the composition, dyes suitable for this invention need not have any other particular properties such as pH dependence, for example. In the context of the present invention, the dyes are used only for assisting the visual perception of the phase separation, and not as indicator dyes.

A key advantage of the invention is the suitability of particularly eco-friendly food dyes.

In a first embodiment, the systems comprise an individual dye, which is soluble only in one of the two solvents, A or B. While the solubilizing effect persists, the solution is coloured blue or green, for example. When the active substance is exhausted, two phases are formed, one of which is colourless while the other is coloured.

In an alternative embodiment, the systems comprise two different dyes, each soluble only in one of the two solvents, A or B. While the solubilizing effect persists, the solution has a hybrid colour; on endpoint indication, the two phases then exhibit different colorations. Suitable systems are reproduced in Table C below, for example:

TABLE C

Solvent/dye systems

| System | Solvent | Dyes | Individual colour | Colour mixture |
|---|---|---|---|---|
| I | Decamethylcyclopentasiloxane | Beta-Carotene | yellow | green |
|  | Dipropylene glycol | Turquoise | blue |  |
| II | Isopropyl myristate | Beta-Carotene | yellow | orange |
|  | Propylene carbonate | Rhodamine EB4 | red |  |
| III | Isopropyl myristate | Turquoise | blue | violet |
|  | Propylene carbonate | Rhodamine EB4 | red |  |
| IV | Isopropyl myristate | Beta-Carotene | yellow | green |
|  | Propylene carbonate | Patent blue | blue |  |

The dyes ought preferably to be selected such that they remain dissolved throughout the time of use (at any stage of evaporation) and do not form any visible particles as a result of precipitation.

The composition may optionally comprise one or more dye stabilizers, such as Neo Heliopan BB, BHT, Ionol or Tinogard Q, for example, in which case the amounts employed may be about 10 to about 50 wt %, based on the dye.

The following dyes are among preferred dyes for the present invention, on account of suitable dissolution properties:

Pinacryptol yellow

ChromaZone Powder Red 47° C.

COPPER CHLOROPHYLL OS 18%

Glowbug Red TH50

Glowbug Turquoise TH40
Macrolex Red EG
Bekro Blue 505-0004
Bekro Red 348-0001
Bekro 74/X2032-6
Bekro 10/X2031-6
Lycopene
Savinyl flame red
Savinyl yellow
Savinyl blue
Solvaperm Blue 2B
Solvaperm Red PFS
Solvaperm Red BB
Solvaperm Red G
Solvaperm Red 2G
Hostasol Red 5B
COLOUR FD&C BLUE #104 (C.I.61568)
COSMETIC COLOUR BLUE VIOLET C.I.60725.
COSMETIC COLOUR TURQUOISE C.I.61565
COSMETIC COLOUR TURQUOISE C.I.61565
BRIGHT YELLOW C.I. 12700
COSMETIC COLOUR BROWN (C.I.12010)
COSMETIC COLOUR BROWN (C.I.12010)
BLUE C.I.61554
COSMETIC COLOUR ALIZARIN BRILLANT VIOLET R (C.I.60730)
COLOUR BLACK C.I.77266
Rhodamine EB4 C.I.45100
COSMETIC COLOUR PHLOXIN C.I.45410
D&C RED NO. 33 C.I.17200
D & C ORANGE NO. 4/C.I.15510
ORANGE II (BLOOD ORANGE, C.I.15510)
Green (C.I.74260)
D & C GREEN NO. 5 C.I.61570
COSMETIC COLOUR URANIN C.I.45350
YELLOW (C.I.11680)
METANIL YELLOW C.I.13065 (ACID YELLOW 36)
COSMETIC COLOUR BLUE C.I.74160
DRAGOCOLOUR PATENT BLUE VF ACID BLUE 1 CI 42045
Cosmetic Colour acid blue 7, C.I.42080
COSMETIC COLOUR BLUE (C.I.61585)
FOOD COLOUR YELLOW IRON OXIDE E172/C.I.77492
FOOD COLOUR AZORUBINE LAKE E122/C.I.14720 powder
FOOD COLOUR YELLOW ORANGE LAKE E110/C.I.15985
FOOD COLOUR QUINOLINE YELLOW LAKE E104/C.I.47005
FOOD COLOUR TARTRAZINE LAKE E102/C.I.19140
FOOD COLOUR INDIGOTIN LAKE E132/C.I. 73015
FOOD COLOUR CARMINE RED E120/C.I.75470 POWDER
FOOD COLOUR ENOCYANIN E163
FOOD COLOUR CHLOROPHYLL (COPPERED) E141
FOOD COLOUR CHLOROPHYLL (COPPERED) E141
FOOD COLOUR BETA-CAROTENE.E160A
FOOD COLOUR ANNATTO YELLOW E160b/C.I.75120
FOOD COLOUR DRY COLOUR E150c
FD & C GREEN NO. 3(C.I.42053)
FOOD COLOUR BRILLIANT ACID GREEN E142
D & C YELLOW NO. 10(C.I.47005)
FD&C YELLOW NO. 6 (C.I. 15985) E 110
FD&C YELLOW NO. 5 C.I.19140
COSMETIC COLOUR FAST YELLOW C.I.13015
FOOD COLOUR GREEN 114 (E102+E133)
FOOD COLOUR COFFEE BROWN E110+E102+E151+E124
FOOD COLOUR GOLD BROWN (E102,E110,E151)
FOOD COLOUR BROWN (E102,E122,E151)
FOOD COLOUR BRILLIANT BLUE FCF E133/C.I.42090
COSMETIC COLOUR RED C.I. 12490
RED C.I.28160
COSMETIC COLOUR BRILLANT PINK (C.I.18050)
COSMETIC COLOUR YELLOW E(C.I.18965)
SANDOLAN WALKBLAU N-BL (C.I.61585)
COSMETIC COLOUR BLUE GREEN C.I.61570
GREEN POV FLUORESCENT (C.I.42090,59040)
COSMETIC COLOUR PINE NEEDLE GREEN (C.I.19140,42090)
COSMETIC COLOUR MAY GREEN C.I.47005,61570
GREEN YELLOW FLUORESCENT C.I.59040
COSMETIC COLOUR DIAMOND YELLOW fluorescent C.I.45350
COSMETIC COLOUR BLUE PASTE C.I.42051
COSMETIC COLOUR PATENT BLUE (C.I.42090)
PATENT BLUE (C.I.42045)
FOOD COLOUR BLACK
FOOD COLOUR JET BLACK (E151+E110+E102)
COLOUR BLACK C.I.77266
FD & C RED NO. 4, C.I.14700 Z
SYMCOLOR SPIRULINA
Symcolor FOOD COLOUR Paprika extr. E160C
Symcolor Paprika extr. 100.000FE
D&C Green No. 6 C.I.61565
D&C RED NO. 17/C.I. 26100
Symcolor FOOD COLOUR Annatto extr. C.I. 75120 E160B
Symcolor FOOD COLOUR Lutein 10% E161B C.I. 75136
D&C RED NO. 30 C.I.73360
FOOD COLOUR CHLOROPHYLLIN, coppered E141
FOOD COLOUR LEMON YELLOW E102
COLOUR ALLURA RED AC 85% E129
FOOD COLOUR BRILLIANT BLACK BN (E151/C.I.28440)
FD&C BLUE NO. 1 C.I.42090 WITH E 133
FOOD COLOUR PONCEAU 4R E124/C.I.16255
FOOD COLOUR INDIGOTIN E132 C.I.73015
FOOD COLOUR TARTRAZINE E102/C.I.19140
FD&C RED NO. 40 C.I.16035 CERTIFIED
FOOD COLOUR PATENT BLUE V(E131/C.I.42051)
FOOD COLOUR AZORUBINE (E122/C.I.14720)
FOOD COLOUR AMARANTH (E123/C.I.16185)
FOOD COLOUR YELLOW ORANGE E110/C.I.15985
FOOD COLOUR QUINOLINE YELLOW/E104/C.I.47005
Beta-Carotene
Azorubine
Rhodamine EB4

Release Mechanisms

The systems of the present invention comprise preferably—but not exclusively—room freshener systems, examples being so-called membrane air fresheners, electric air fresheners, wick air fresheners, rattan rod air fresheners, and the like. They are usually made available in receptacles or containers, which are fabricated from glass, ceramic or else plastic, and are either wholly or partly transparent. Any such container may also be opaque in principle, but contain a window through which the endpoint indication can be monitored.

A feature common to the systems is that they must have a mechanism which allows the active substance, in other words preferably the fragrance, to be delivered to the ambient surroundings, but which prevents the escape to any notable extent of other volatile components, such as, for example, the solvents or else, in certain circumstances, the dyes.

In a first embodiment of the invention, the mechanism for release of the active ingredient, but for retention of the further volatile constituents, comprises a semi-permeable polymeric membrane.

In a further embodiment of the invention, the mechanism for release of the active ingredient, but for retention of the further volatile constituents, comprises wood. More specifically, the container is made of glass, ceramic or plastic and has a narrow opening inserted into which there are wooden rods, made from rattan, for example. On account of the capillary forces, the fragrances penetrate the wooden rods and are given off to the ambient air, while the less volatile solvents remain—optionally as a result of adjustment to the rheology by addition of thickeners. Particular care should be taken here to ensure that in the event of additional dye indication, the dyes are selected so that they exhibit little or no diffusion into the wood.

The systems of the invention can be stored before solvent or fragrance are given off to the air. The storage period may be at least one day, preferably at least one week, more preferably at least one month, and especially preferably at least one year. The temperature during storage may be between 0 and 50° C., preferably between 15 and 30° C. It is not necessary here to maintain a constant temperature. In the preferred embodiment of the invention, the odour of the mixture and/or the colour is unchanged during storage. In order to assess a change in colour and/or a change in odour, use may be made in particular of the Duo-Trio Test according to DIN EN ISO 10399:2010-06.

INDUSTRIAL APPLICABILITY

The invention further provides a method for optical endpoint display for an active release system, in which two solvents, A and B, which are immiscible or only minorly miscible with one another are placed in a suitable container, and a suitable solubilizing active ingredient is added in an amount such as to form a single-phase preparation, the exhaustion of the quantity of fragrance being indicated by the loss of the solubilizing effect and the separation of the phases.

In two embodiments of the method that are preferred independently of one another, it is possible for the preparations to be admixed (i) with a dye which is soluble only in one of the two solvents, A or B, so that the endpoint indication by phase separation is assisted by formation of a colourless phase and a coloured phase, or (ii) with two different dyes, each soluble only in one of the two solvents, A or B, so that the endpoint indication by phase separation is assisted by formation of two different-coloured phases.

The invention lastly provides the use of the system outlined above as an indicator for monitoring the temporal profile of physical and/or chemical processes, such as the evaporation of a volatile compound, especially of a fragrance, for example.

EXAMPLES

Examples 1 to 4

Figure 1:
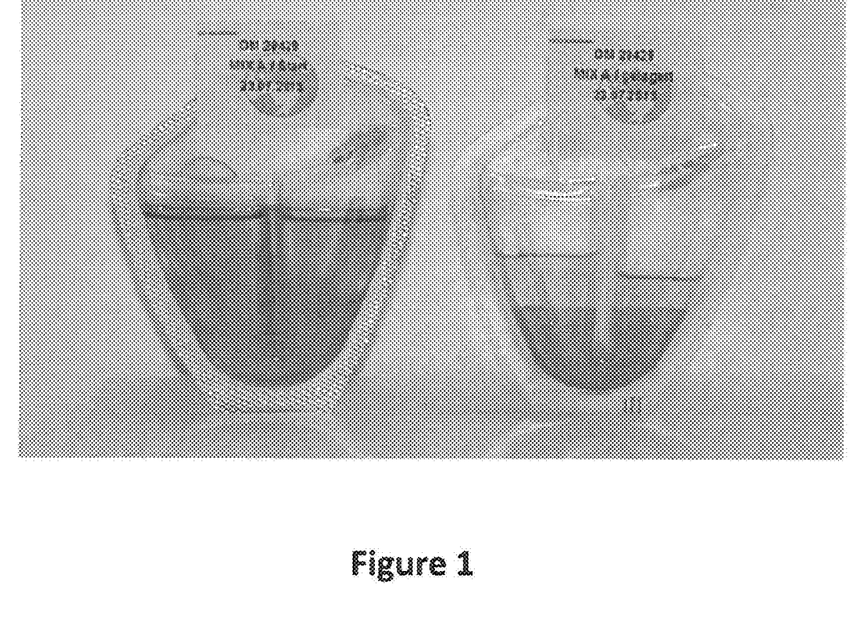
FIG. 1 illustrates a system according to Example 1.
Figure 2:
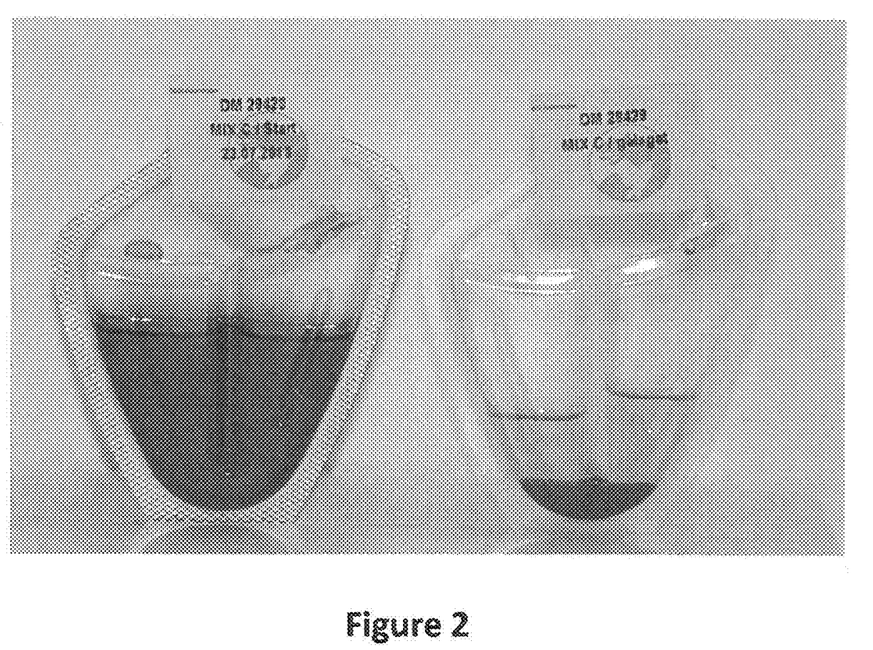
FIG. 2 illustrates a system according to Example 2.
Figure 3:
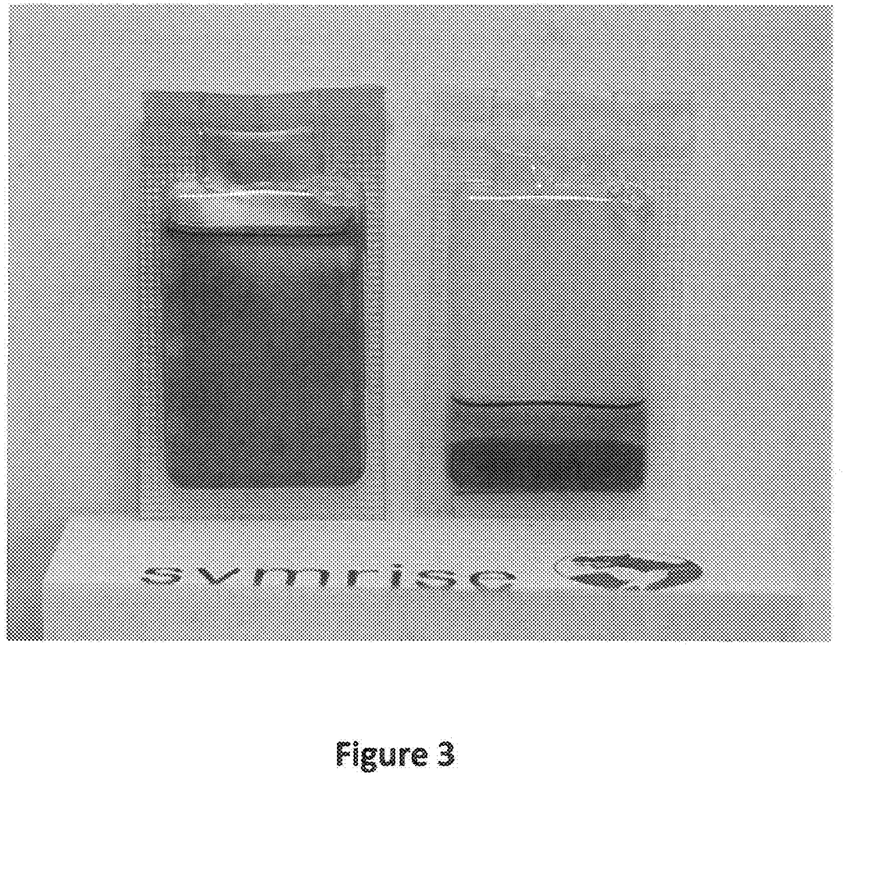
FIG. 3 illustrates a system according to Example 3.
Figure 4:
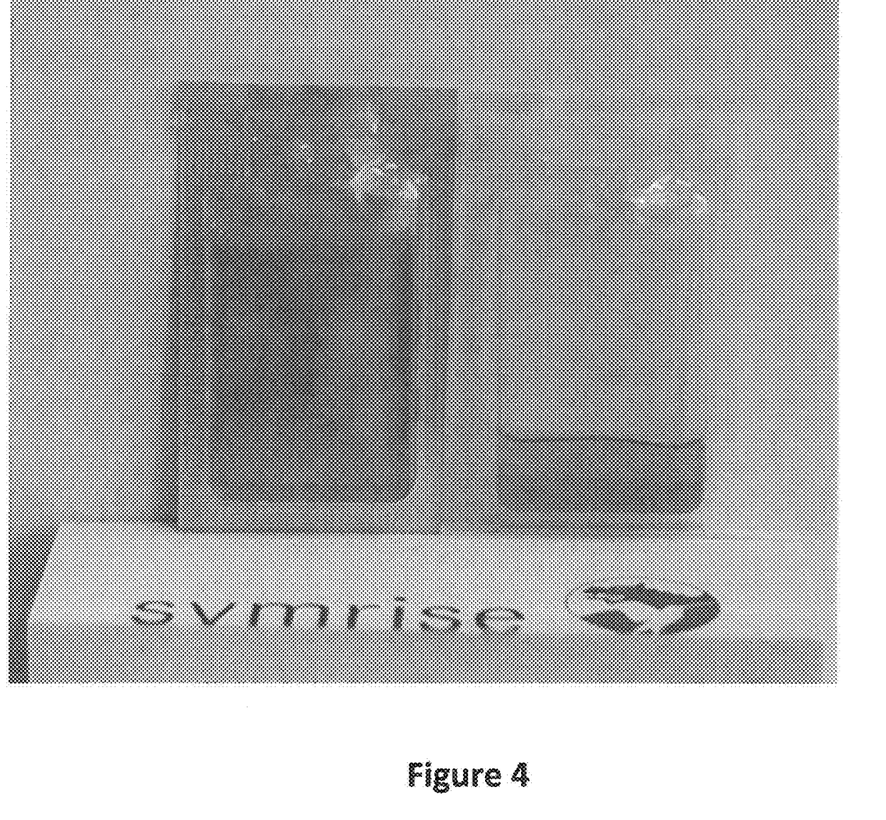
FIG. 4 illustrates a system according to Example 4.

4 different systems were produced. Two specimens of each composition were produced. One specimen served as the "starting point"; it was stored in a refrigerator and not opened. The second specimen served as the "endpoint"; this specimen was opened and evaporated. The composition of the powders is shown in Table 1. A visual reproduction of the specimens in the original state (single phase) and after attainment of the endpoint is found in FIGS. 1 to 4.

TABLE 1

| Composition of the formulations | | | | |
|---|---|---|---|---|
| Components | 1 | 2 | 3 | 4 |
| Solvents | | | | |
| Propylene carbonate | 3.0 | 1.5 | — | — |
| Isopropyl myristate | 1.5 | 1.5 | — | 2.0 |
| Decamethylcyclopentasiloxane | — | — | 4.0 | — |
| Dipropylene glycol | — | — | 1.0 | 4.0 |
| Fragrances | | | | |
| Citral | 0.5 | 0.5 | — | — |
| Phenyl acetate | 4.0 | 4.0 | — | — |
| Limonene | 2.0 | 2.0 | — | — |
| Hexyl acetate | 1.0 | 1.0 | — | — |
| Apfel CC (contains 20% DPG) | — | — | 15.0 | — |
| Exotic Mango New | — | — | — | 14.0 |
| Dyes | | | | |
| Beta-Carotene | 0.05 | 0.05 | 0.05 | 0.05 |
| Azorubine | 0.05 | — | — | — |
| Patent blue | — | 0.05 | — | — |
| Turquoise | — | — | 0.05 | — |
| Rhodamine EB4 | — | — | — | 0.05 |

The invention claimed is:

1. An active ingredient release system with optical endpoint display, comprising
   (a) a container for accommodating the components,
   (b) two solvents A and B located therein, which are immiscible or only minorly miscible with one another,
   (c) at least one volatile active ingredient which serves as solubilizer for the solvents A and B to obtain a single phase preparation wherein the exhaustion of the active ingredient by release into the environment is indicated by the loss of the solubilizing effect and the separation of the phases A and B, and
   (d) a mechanism which allows the release of the active ingredient into the environment, but restrains the other volatile constituents of the composition.
   wherein said active ingredient represents fragrance, active antimicrobial ingredient and/or insect repellent.

2. The system according to claim 1, comprising solvents selected from the group consisting of $C_6$-$C_{22}$ fatty acid $C_1$-$C_6$ alkyl esters, $C_1$-$C_6$ alkyl carbonates, $C_2$-$C_4$ alkylene glycols and siloxanes.

3. The system according to claim 1, comprising as solvent combinations, decamethylcyclopentasiloxane/dipropylene glycol or isopropyl myristate/propylene carbonate.

4. The system according to claim 1, comprising as active ingredients, fragrances selected from the group consisting of aldehydes, ketones, acetals, ketals and silicic esters and mixtures thereof.

5. The system according to claim 1, comprising solvent/active ingredient combination, a propylene carbonate/isopropyl alcohol solvent mixture in combination with at least one of the active ingredients citral, phenyl acetate, limonene and hexyl acetate.

6. The system according to claim 1, further comprising stabilizers.

7. A system according to claim 1, further comprising a dye which is soluble only in one of the two solvents, A or B.

8. A system according to claim 1, further comprising two different dyes, each of which is soluble only in one of the two solvents, A or B.

9. A system according to claim 1, wherein said mechanism comprises a semi-permeable polymeric membrane.

10. A system according to claim 1, wherein said mechanism comprises wood.

11. A method for optical endpoint display for an active release system comprising the steps of
placing two solvents, A and B, which are immiscible or only minorly miscible with one another, in a suitable container, and
adding a suitable solubilizing active ingredient in an amount to form a single-phase preparation,
wherein the exhaustion of the active ingredient by release into the environment is indicated by the loss of the solubilizing effect and the separation of the phases.

12. The method according to claim 11, wherein the preparation is admixed with a dye which is soluble only in one of the two solvents, A or B, so that the endpoint indication is supported by phase separation through the formation of a colourless phase and a coloured phase.

13. The method according to claim 11, wherein the preparation is admixed with two different dyes, each of which is soluble only in one of the two solvents. A or B, so that the endpoint indication is assisted by phase separation through formation of two different-coloured phases.

14. A system according to claim 1, wherein the solvents A and B are selected from the group consisting of vegetable oils, $C_6$-$C_{22}$ fatty acid $C_1$-$C_6$ alkyl esters, $C_1$-$C_6$ alkyl carbonates, $C_2$-$C_4$ alkylene glycols and siloxanes and mixtures thereof.

15. A system according to claim 14, wherein the solvents A and B are selected from the group consisting of esters of lauric acid, myristic acid and stearic acid with ethanol, propanol or isopropyl alcohol, ethylene carbonate, propylene carbonate, butylene carbonate, ethylene glycol, propylene glycol, diethylene glycol, dipropylene glycol and decamethylcyclopentasiloxane and mixtures thereof.

16. A system according to claim 1, wherein the mixing ratio of solvents A:B is situated in a range between about 40:60 and 60:40 parts by weight.

17. A system according to claim 1, wherein the mixing ratio of solvents A:B is about 50:50 parts by weight.

* * * * *